United States Patent
Bar

(10) Patent No.: US 11,839,910 B2
(45) Date of Patent: Dec. 12, 2023

(54) INSECT-BASED BIOWASTE PROCESSING APPARATUS

(71) Applicant: YB INSECT FARMING LTD, Kibutz Be'erot Yitzhak (IL)

(72) Inventor: Yaniv Bar, Tel-Aviv (IL)

(73) Assignee: YB INSECT FARMING LTD, Kibutz Be'erot Yitzhak (IL)

( * ) Notice: Subject to any disclaimer, the term of this patent is extended or adjusted under 35 U.S.C. 154(b) by 78 days.

(21) Appl. No.: 17/617,179

(22) PCT Filed: Jun. 15, 2020

(86) PCT No.: PCT/IL2020/050661
§ 371 (c)(1),
(2) Date: Dec. 7, 2021

(87) PCT Pub. No.: WO2020/255121
PCT Pub. Date: Dec. 24, 2020

(65) Prior Publication Data
US 2022/0314288 A1 Oct. 6, 2022

(30) Foreign Application Priority Data
Jun. 17, 2019 (IL) .......................................... 267413

(51) Int. Cl.
*B09B 3/60* (2022.01)
*A01K 67/033* (2006.01)
(Continued)

(52) U.S. Cl.
CPC .............. *B09B 3/60* (2022.01); *A01K 67/033* (2013.01); *B09B 2101/25* (2022.01); *B09B 2101/70* (2022.01); *B09B 2101/85* (2022.01)

(58) Field of Classification Search
CPC .... A01K 67/033; B09B 3/60; B09B 2101/25; B09B 2101/70; B09B 2101/85
See application file for complete search history.

(56) References Cited

U.S. PATENT DOCUMENTS

| 2,994,592 A | 8/1961 | Scovel et al. |
| 4,334,498 A * | 6/1982 | Bedding .............. A01K 67/033 |
| | | 119/6.7 |

(Continued)

FOREIGN PATENT DOCUMENTS

| CN | 102351394 A | 2/2012 |
| CN | 103145466 A | 6/2013 |

(Continued)

OTHER PUBLICATIONS

Office action from the Chinese patent office in a counterpart foreign application—Chinese Patent Application No. 202080044583.1 dated Dec. 2, 2022 (6 pages) and English machine translation (2 pages).

(Continued)

*Primary Examiner* — Monica L Perry
*Assistant Examiner* — Aaron M Rodziwicz
(74) *Attorney, Agent, or Firm* — Roach Brown McCarthy & Gruber, P.C.; Kevin D. McCarthy

(57) ABSTRACT

Continuous insect-based biowaste processing apparatus has a tubular drum; a drive for rotatably driving the drum; a shaftless screw conveyor fixedly connected to an inner surface of the drum; circumferentially spaced cantilevered blades that (a) are connected to the inner drum surface and (b) each longitudinally extends throughout the drum; and a mechanism for introducing a conglomerate portion that includes biowaste and insect larvae into the drum interior. The screw conveyor is subdivided into longitudinally spaced chambers for the introduced insect larvae, each of the chambers being defined by two adjacent flights of the screw conveyor and by the blades. The size of the insect larvae progressively increases within a more distally located rearing chamber. Two or more blades firmly hold and unify the conglomerate portion throughout its residing time within the drum interior while being distally conveyed.

19 Claims, 9 Drawing Sheets

(51) Int. Cl.
  *B09B 101/85* (2022.01)
  *B09B 101/25* (2022.01)
  *B09B 101/70* (2022.01)

(56) References Cited

U.S. PATENT DOCUMENTS

| | | |
|---|---|---|
| 2011/0293392 A1 | 12/2011 | Ekholm |
| 2015/0296760 A1 | 10/2015 | Perednia |
| 2017/0226023 A1 | 8/2017 | Wang |
| 2018/0065152 A1* | 3/2018 | Hasa ................. B07B 1/24 |
| 2020/0008408 A1* | 1/2020 | Jansen ............... A01K 1/0082 |
| 2020/0375161 A1* | 12/2020 | Emery ............... B23Q 7/003 |
| 2022/0183261 A1* | 6/2022 | Gray ................. A01K 61/54 |
| 2022/0306404 A1* | 9/2022 | De Wolf ............ A01K 67/033 |

FOREIGN PATENT DOCUMENTS

| | | |
|---|---|---|
| CN | 203333503 U | 12/2013 |
| CN | 104311178 A | 1/2015 |
| CN | 105016802 A | 11/2015 |
| EP | 2477747 B1 | 3/2019 |
| FR | 3003560 A1 | 9/2014 |
| FR | 3070002 A1 * | 2/2019 |
| JP | 2015221724 A | 12/2015 |
| WO | WO-2018169398 A1 * | 9/2018 ........... A01K 1/0082 |
| WO | WO-2019211511 A1 * | 11/2019 ............... A01K 1/00 |
| WO | WO-2020129058 A1 * | 6/2020 ........... A01K 67/033 |

OTHER PUBLICATIONS

International Search Report for PCT/IL2020/050661; dated Sep. 9, 2020 (3 pages).
Written Opinion of the International Searching Authority for PCT/IL2020/050661; dated Sep. 9, 2020 (4 pages).

* cited by examiner

INSECT-BASED BIOWASTE PROCESSING APPARATUS

FIELD OF THE INVENTION

The present invention relates to the field of biological processors. More particularly, the invention relates to insect-based biowaste processing apparatus.

BACKGROUND OF THE INVENTION

The disposal or the processing of the steadily increasing amounts of organic waste material, such as sewage sludge and food waste, hereinafter referred to as "biowaste", is a major challenge confronting municipalities, industrialized markets and nations.

Insect larvae have recently been targeted as effect means for processing biowaste since they can consume up to twice their body weight each day, allowing biowaste to be converted into insect protein. The insect protein and lipids are then able to be fed to various animals such as chickens and fish. Some insect larvae have a relatively high energy value, depending on their fat content. Additionally, the solid and liquid waste that the insect larvae may produce can be used as a fertilizer. Another significant benefit of feeding biowaste to insect larvae relates to their ability of inactivating disease-transmitting bacteria normally associated with the biowaste.

Some attempts have been made for utilizing insect larvae to process biowaste on a mass scale.

In one method, insect larvae are introduced into flat trays or containers. Since insect larvae require an adequate supply of air, they tend to remain at a distance of 10-30 cm from the upper surface of a pile of biowaste that is periodically added. This method is deficient since the flat trays or containers are configured with a maximum height of 30-40 cm, leading to poor operational surface utilization. Also, insect larvae avoid a significant amount of the biowaste that is not exposed to an air supply, resulting in anaerobic decomposition of the biowaste, malodorous conditions and undesirable byproducts. Moreover, there are difficulties involved with temperature regulation within the flat trays and containers due to the metabolic heat generated by the larvae and the anaerobic decomposition. When the internal temperature becomes significantly greater than 35° C., the insect larvae crawl away or even die, and therefore the biomass processing efficiency is severely lacking.

In another method, a drum containing the insect larvae and biowaste is rotated, to facilitate mixing and aeration of the insect larvae and biowaste, as well as dissipation of the generated heat. However, the drum is rotated at an excessively high rate, CN 102351394 for example disclosing a speed of one revolution per 10 minutes, which limits metabolic activity of the insect larvae. The insect larvae therefore have to be retained within the drum for an extended period of time substantially equal to their larval lifetime until they develop to the prepupal stage. Since all insect larvae are of substantially a same age and size and are discharged at the same time, the drum cannot function as a substantially continuous processor due to the significant delay time between the introduction time of the young larvae and the discharge time of the developed larvae, and therefore insect protein is not readily available at all times. Additional drawbacks of this prior art method include the limited volume of biowaste that is processed per load and the lack of automation.

It is an object of the present invention to provide substantially continuous insect-based biowaste processing apparatus.

It is an additional object of the present invention to provide insect-based biowaste processing apparatus whose rate of processing biowaste is relatively high.

It is another object of the present invention to provide insect-based biowaste processing apparatus that is automated.

Other objects and advantages of the invention will become apparent as the description proceeds.

SUMMARY OF THE INVENTION

A substantially continuous insect-based biowaste processor comprises a tubular drum having a longitudinal axis and an interior; a drive for rotatably driving said drum about said axis; a shaftless screw conveyor fixedly connected to an inner surface of said drum; a plurality of circumferentially spaced cantilevered blades that are connected to said inner drum surface and that each longitudinally extend throughout said drum; and means for introducing a conglomerate portion that includes biowaste and insect larvae into said drum interior, wherein said screw conveyor is subdivided into a plurality of longitudinally spaced rearing chambers for the introduced insect larvae, each of said rearing chambers being defined by two longitudinally adjacent flights of said screw conveyor and by said circumferentially spaced cantilevered blades and within which insect larvae of a substantially uniform developmental stage are retained, wherein two or more of said circumferentially spaced cantilevered blades are configured to firmly hold and unify said conglomerate portion at any given instance throughout its residing time within said drum interior while being distally conveyed, and wherein the insect larvae are progressively more developed within a more distally located rearing chamber.

A fresh supply of conglomerate containing young insect larvae is preferably introducible into a proximal rearing chamber simultaneously with discharge of fully developed insect larvae from a distal rearing chamber.

In one aspect, the biowaste processor further comprises a control system for monitoring parameters of importance that are associated with the conglomerate portion received in one of the rearing chambers and for adjusting a value of one or more of the parameters that has been found to be deviative. A controller in data communication with the drive is configured to regulate a rotational speed of the drum to be no more than one-half a revolution per hour.

DETAILED DESCRIPTION OF THE INVENTION

A substantially continuous insect-based biowaste processor is configured with a drum having a shaftless screw conveyor that is subdivided into a plurality of longitudinally spaced rearing chambers, within each of which insect larvae, particularly Diptera larvae, of a different developmental stage may be retained. A mixture of undeveloped larvae and biomass (hereinafter "conglomerate") is introduced into the drum via an inlet port in communication with a first proximal rearing chamber. During a slow rotation of the drum together with the screw conveyor that maximizes the residing time of the insect larvae within the drum interior, the larvae-bearing conglomerate located in one of the rearing chambers is conveyed along the drum while the insect larvae digest the biomass and consequently become physically developed, until the conglomerate is discharged from a distal end of the drum via an outlet port to allow harvesting of fully developed insect larvae.

The biowaste processor promotes intensive cultivation of insect larvae, and may be configured as a subunit in a large scale facility or as an isolated unit for small-scale operations. A biowaste processing operation may be monitored and controlled by a self-learning module to fully control and maintain an insect mass cultivation process without any human intervention.

Figure 1:
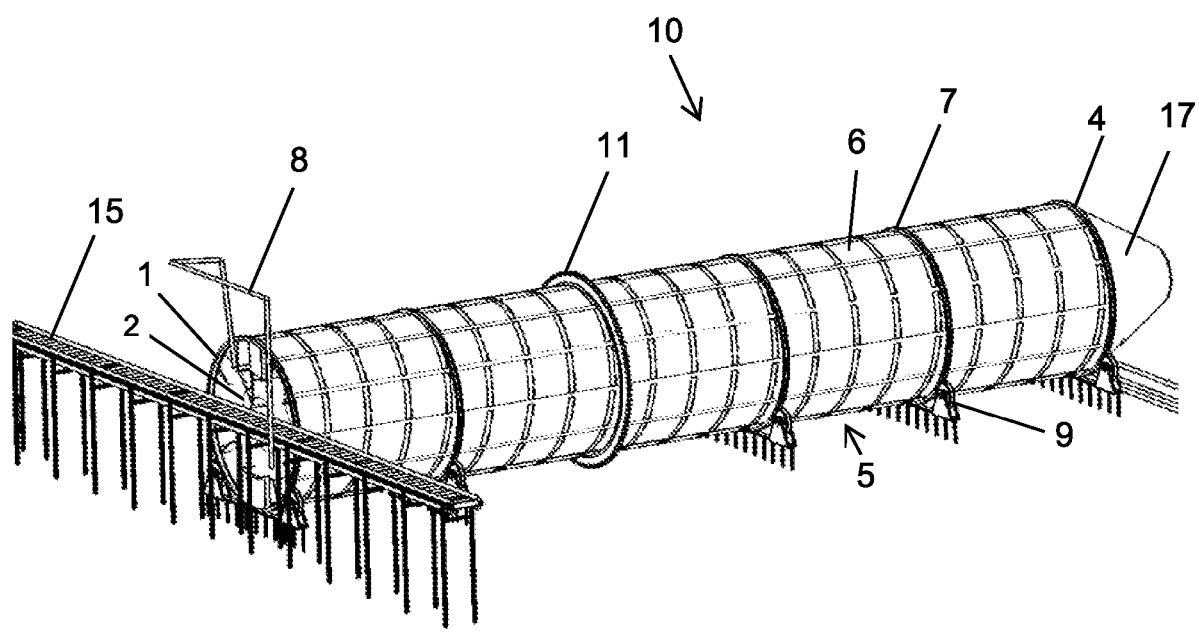
FIG. 1 is a perspective view of an embodiment of a biowaste processor.

FIG. 1 illustrates an embodiment of a biowaste processor, generally indicated by numeral 10. Biowaste processor 10 comprises a tubular drum 5, to the inner surface of which is fixedly connected a shaftless screw conveyor. Drum 5 may be made of glass fiber-reinforced plastic (FRP) for significant reduction in weight relative to any stainless steel alloy and corresponding savings in production and operational costs, although other materials may be used as well. The outer layer of the drum material is preferably blackened to restrict or altogether prevent the transmission of light into the drum interior for the benefit of the photophobic insect larvae. Drum 5 has a proximal inlet end 1 and a distal outlet end 4. Drum 5 preferably has a length ranging from 10-60 m.

The use of a shaftless screw conveyor advantageously avoids the tendency of the conglomerate to adhere to the central shaft of a conventional screw conveyor, and also promotes higher filling rates and low speeds. Additionally, a shaftless screw conveyor does not require any bearings normally needed by a rotating shaft, and therefore facilitates direct introduction of the conglomerate and a reduction in maintenance work.

Larvae-biomass conglomerate is introducible via inlet port 2 which is coincident with the shaftless central region of the screw conveyor. The conglomerate is produced by a mixture of substrate, biowaste and insect larvae. The substrate is generally cellulose-based waste, such as cellulosic urban waste derived from cut branches and grass, wood waste, and paper, which is used in order to regulate the levels of nitric compounds such as ammonia and to absorb excess fluids from the biowaste processing operation. The biowaste is used as food for the insect larvae.

The substrate and biowaste are treated at the entrance to the facility by various pre-processes that may include sterilization, crushing, and storing, to produce a resulting particle size and texture suitable for efficient digestion by the insect larvae. Each pre-process requires dedicated apparatus, and is carried out until achieving a viscous pulp, after which the substrate and biowaste are received in separate reservoirs. Prior to being introduced to drum 5, the substrate and biowaste are delivered by a corresponding pump, e.g. a peristaltic pump, from the corresponding reservoir to a container supported on roller conveyor system 15, which is generally horizontally disposed to facilitate conveyance of the container to the vicinity of inlet port 2. The substrate and biowaste are then mixed together within the container.

Young insect larvae, e.g. 3-5 days old, are diluted in an oxygen-enriched liquid by manually inserting the insect larvae within a tank that is located remotely from drum 5, in order to provide a continuous supply of insect larvae on a daily basis, whether for one processor or for a plurality of processors. The specific concentration of the insect larvae is dependent upon the number of processors that are operational. Generally speaking, the minimum concentration of insect larvae ranges from 40 to 70 thousand larvae per cubic meter in order to ensure cost effective operation of biowaste processor 10. It will be appreciated that the insertion of insect larvae within the tank prior to delivery to the drum is the only action related to the processing operation that involves manpower, and even this action is performed remotely to the drum.

The mixture of oxygen-enriched liquid and insect larvae is delivered by a larvae delivery mechanism, e.g. a pneumatic mechanism, to a region that is proximate to the container supported on roller conveyor system 15, and is then discharged by sprinklers onto the upper surface of the substrate and biowaste mixture located within the container prior to being introduced into inlet port 2. The larvae may be added to the substrate-biowaste mixture at a density of approximately 4 larvae per $cm^2$ of mixture to form the conglomerate. Afterwards, the formed conglomerate is delivered by a peristaltic pump, or by any other suitable delivery mechanism, to inlet port 2. The insect larvae are then able to digest the biomass and increase in size.

The percentage of the substrate and of the biowaste within the conglomerate is determined based on the relative liquid content of the substrate and biowaste. For example, if the biowaste is sludge derived from a municipal source having a 75% liquid content, the percentage of the substrate should be 60-80% of the conglomerate. If the waste has low liquid content, e.g. dry manure, the substrate should constitute 30-40% of the conglomerate.

Figure 7:
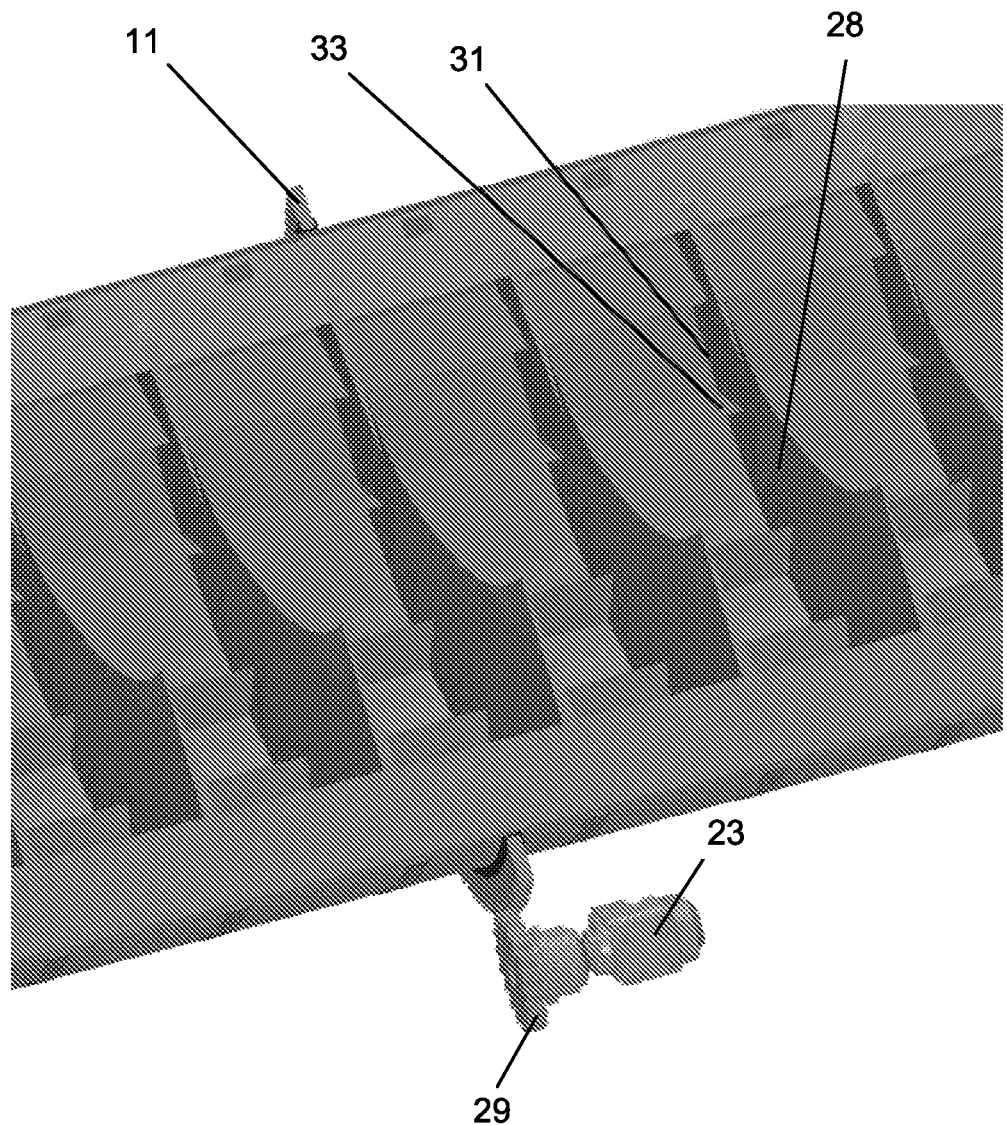
FIG. 7 is an oblique perspective view of a vertical cross section of a central section of the biowaste processor of FIG. 1, showing the connection between the shaftless screw conveyor and a plurality of cantilevered blades as well as a drive unit.

A plurality of longitudinally spaced rings 7 fixed to the outer surface 6 of drum 5 are rotatably supported from below by a corresponding pair of laterally spaced roller wheels 9. A geared ring 11 is fixed to a longitudinally central region of the outer surface 6 of drum 5, and is rotatably driven by the gear 22 of a motor drive 29 shown in FIG. 7 configured to rotate drum 5 at a predetermined slow rate of no more than one-half a revolution per hour, generally ranging from 1-10 revolutions per day, which is dependent upon the duration of the growth cycle of the insect larvae being harvested by processor 10. Rings 7 and 11 are generally concentric to the tubular outer surface 6 of drum 5, while the various flights of the screw conveyor are positioned at an angle thereto.

Figure 2:
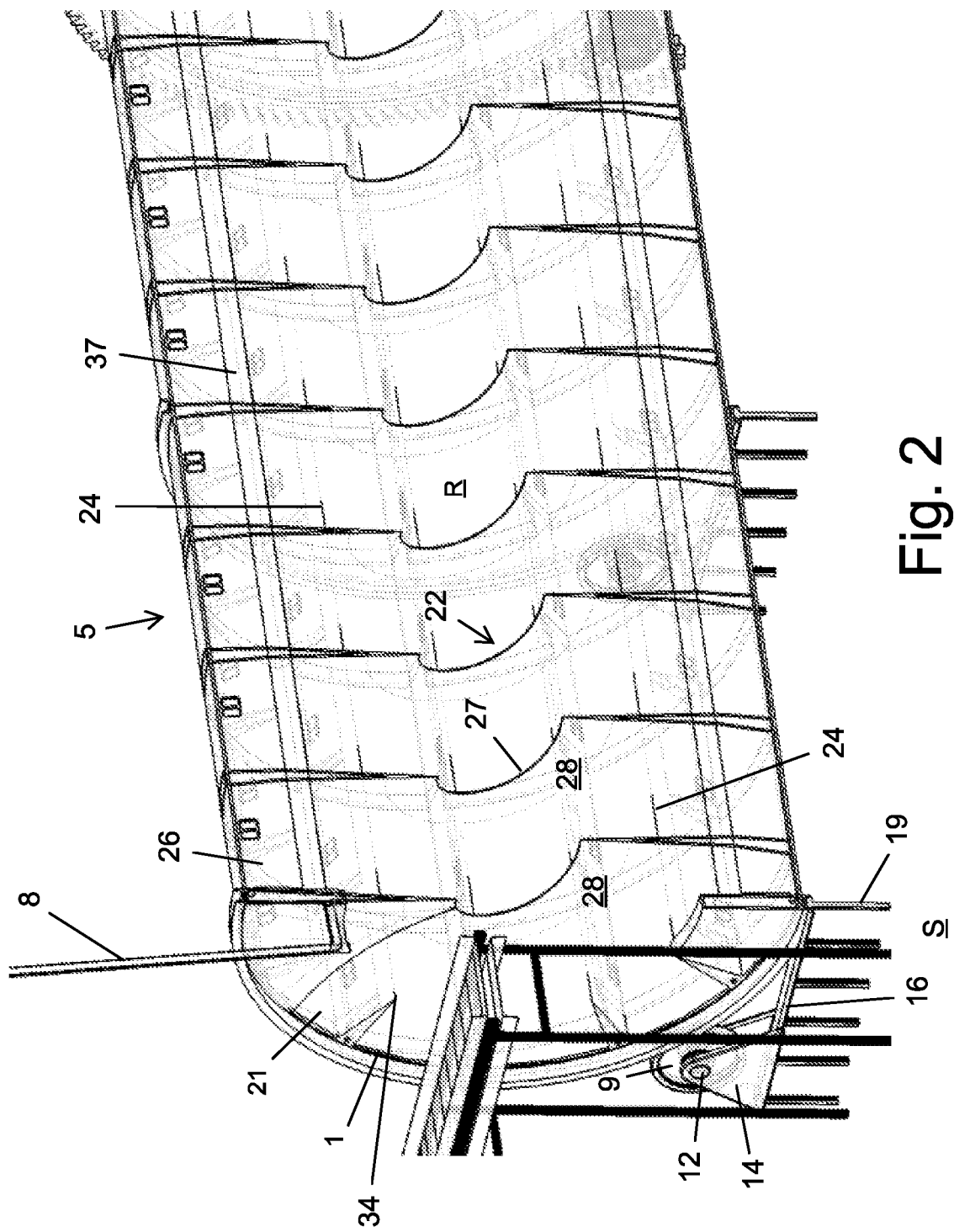
FIG. 2 is a perspective view of a vertical cross section of a proximal section of the biowaste processor of FIG. 1.

As shown in FIG. 2, each roller wheel 9 may rotate in response to rotate of drum 5 about a substantially horizontally oriented and longitudinally extending pin 12, which is fixed to two longitudinally spaced forks 14, e.g. triangularly shaped. The bottom side of each fork 14 may be connected to a horizontal support plate 16 which may be elevated from the underlying surface S by a plurality of laterally spaced vertical rod legs 19.

Figure 3:
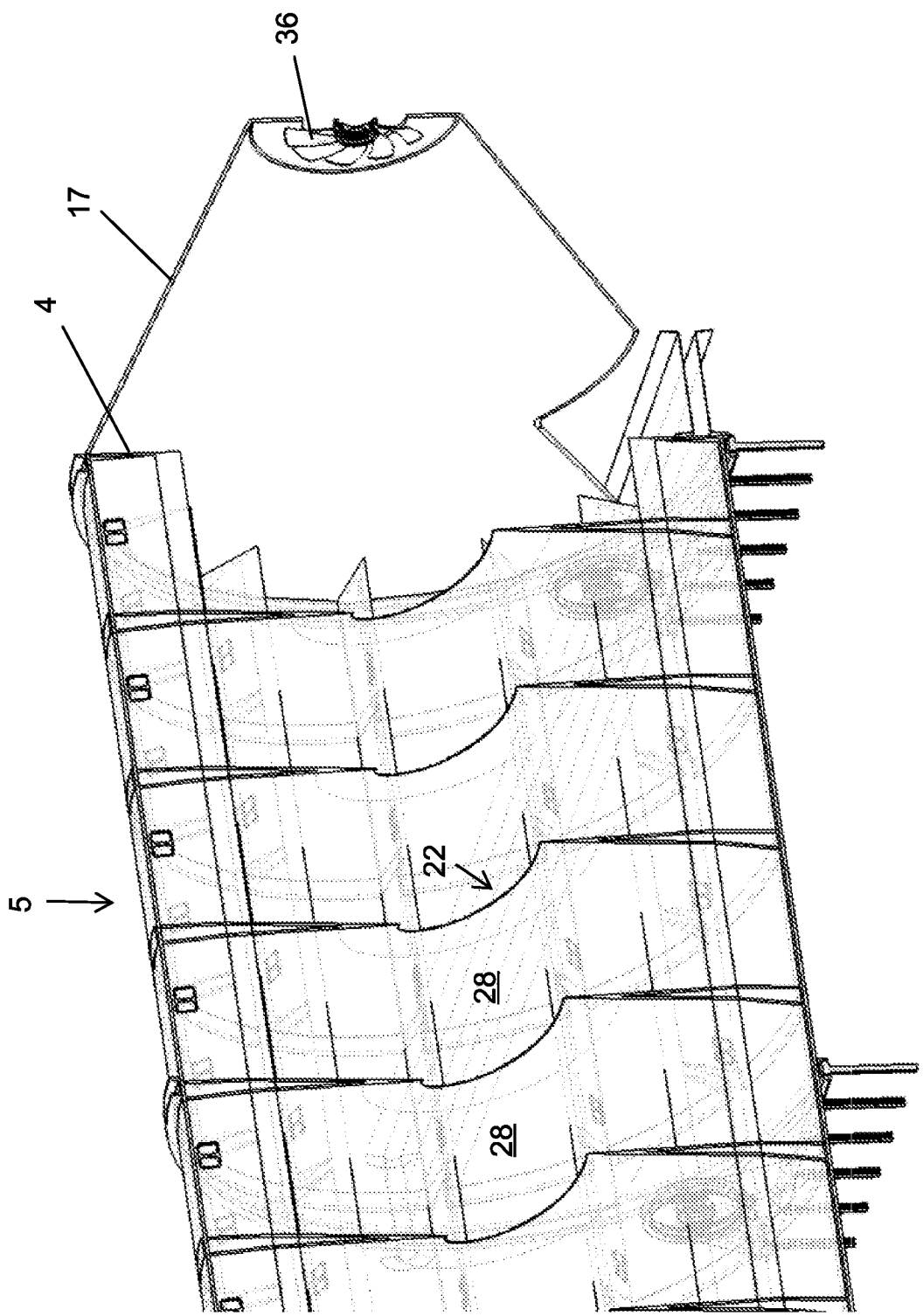
FIG. 3 is a perspective view of a vertical cross section of a distal section of the biowaste processor of FIG. 1.
Figure 4:
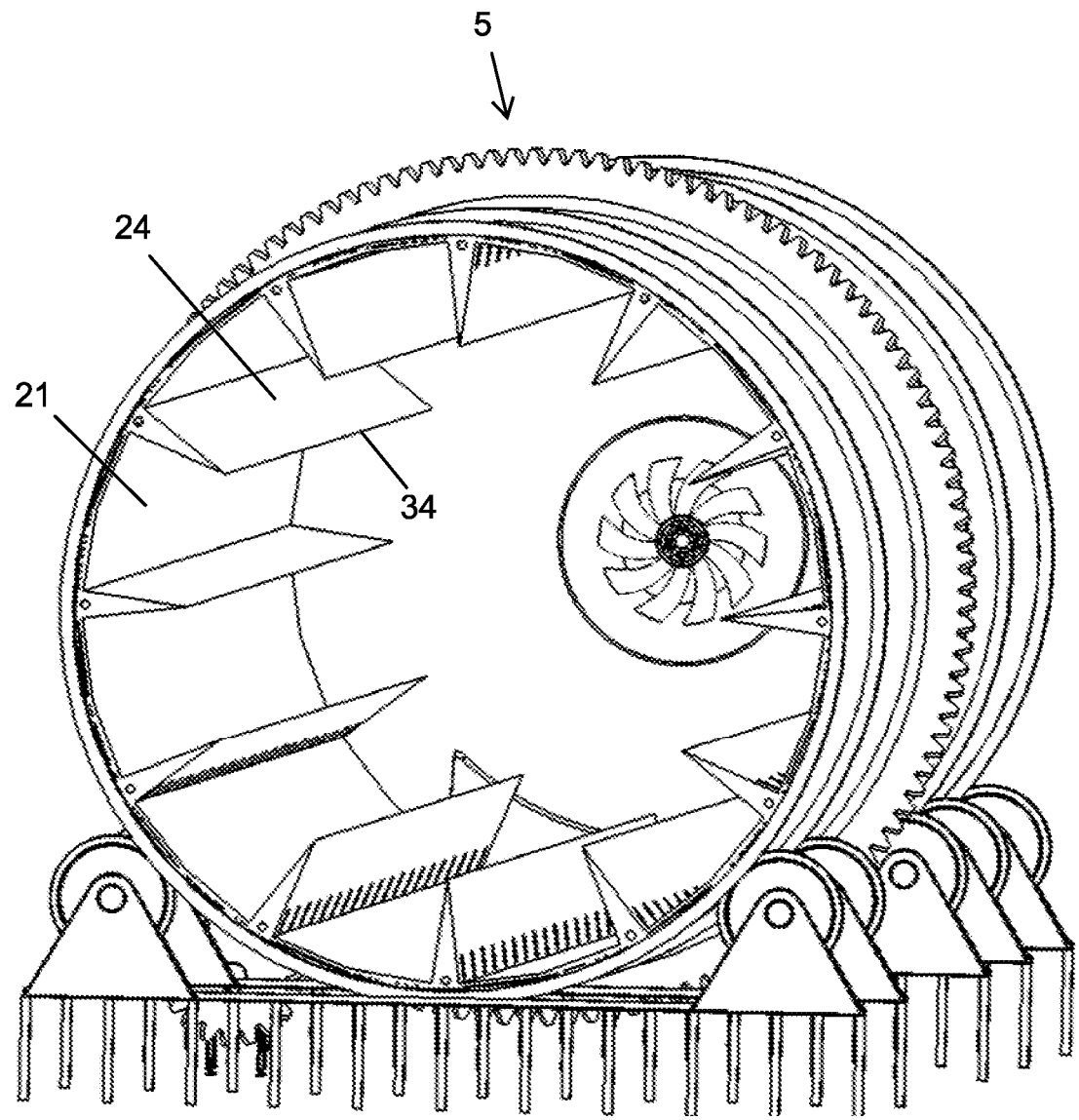
FIG. 4 is a perspective view from a proximal end of the biowaste processor of FIG. 1, shown without the screw conveyor.
Figure 5:
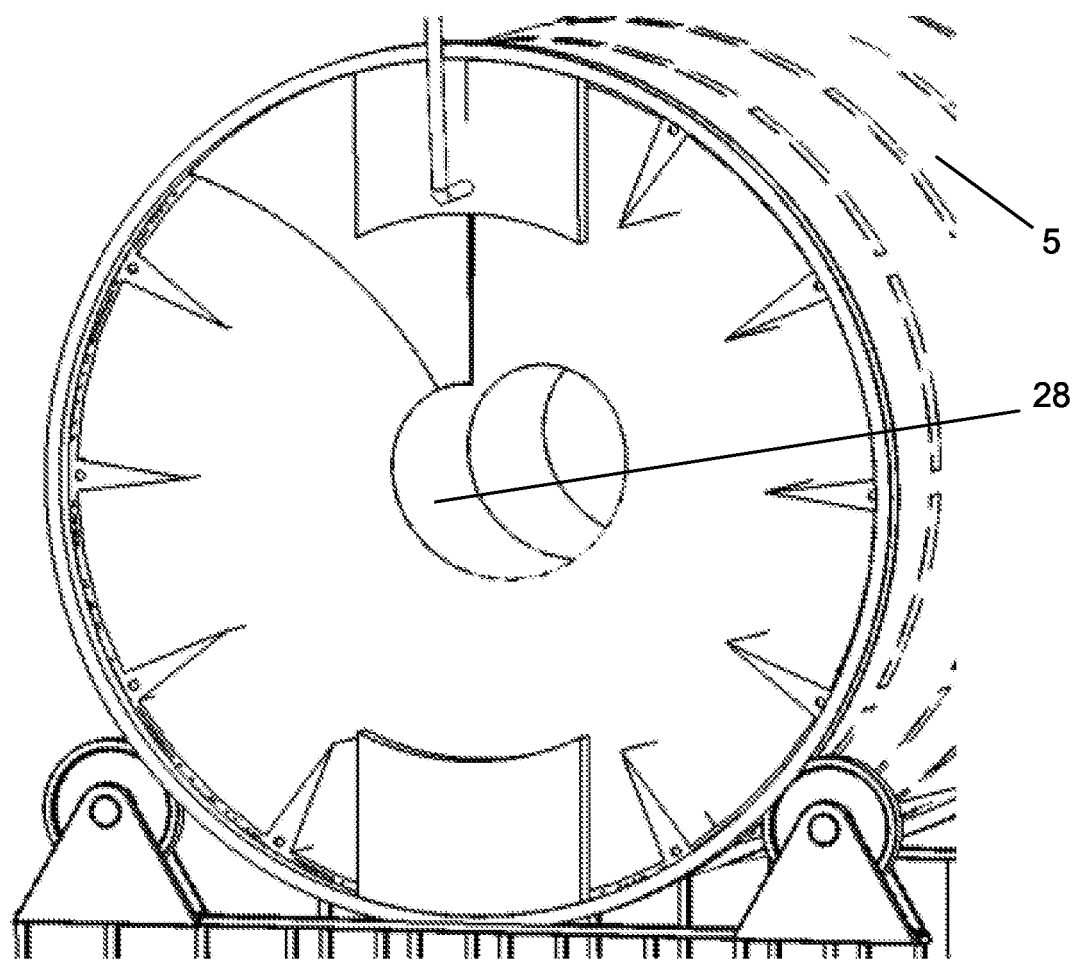
FIG. 5 is a perspective view from a proximal end of the biowaste processor of FIG. 1, shown with the screw conveyor.
Figure 6:
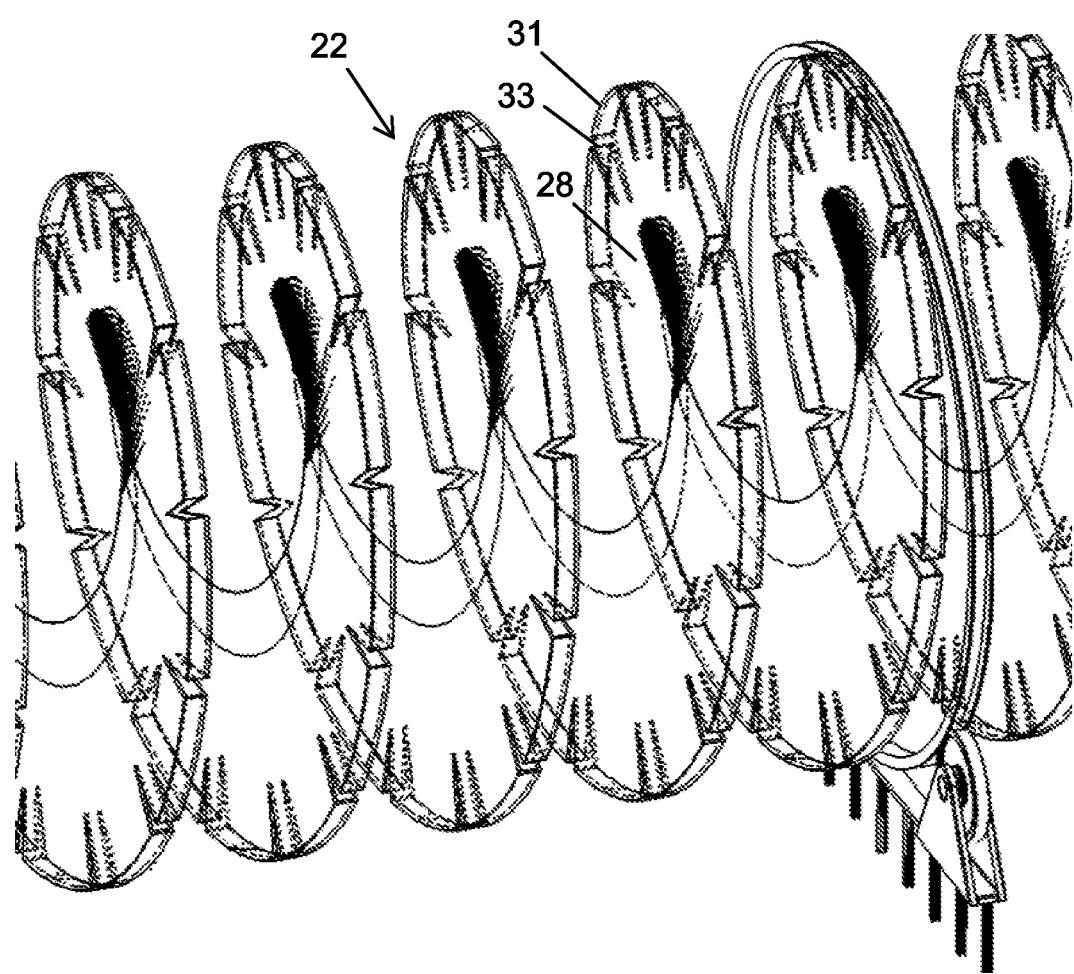
FIG. 6 is a perspective view of a screw conveyor used in conjunction with the processor of FIG. 1.

Referring back to FIG. 1, an air feed tube 8, shown to assume a rectangular configuration, is positioned in fluid communication with inlet end 1 of drum 5, to ensure a reliable influx of air to the conglomerate and to therefore induce discharge of unwanted gas that are derived from the conglomerate. One end of air feed tube 8 is connected to a compressor fixed to the underside of roller conveyor system 15. A distally narrowing shroud 17 within which is housed a fan 36 for expelling unwanted gases from the interior of drum 5 is fixed to outlet end 4 of drum 5, as shown in FIG. 3.

The structure of drum 5 and of shaftless screw conveyor 22 is illustrated in FIGS. 2-7.

A plurality of circumferentially spaced reinforcement beams 24, e.g. twelve beams, are connected to the inner thin-wall surface 21 of drum 5, and longitudinally extend through the length of the drum, from inlet end 1 to outlet end 4. Each beam 24 may have a triangular section, such that its base is connected to inner surface 21 and its cantilevered triangular blade 34 is positioned within the drum interior, to provide a firm hold onto the introduced conglomerate as drum 5 rotates. Additionally, the triangular blades 34 are adapted to direct the conglomerate, particularly following rotational displacement, to a central region of a rearing chamber and to prevent passage thereof to a neighboring rearing chamber.

The triangular blades 34, which may be configured similarly to a plow tooth, may be extensions of, and connected to, the longitudinal beams 24. Alternatively, each triangular blade 34 may be integrally formed with a corresponding beam 24.

In one embodiment, each reinforcement beam 24 having a triangular cross section has a hollow interior cavity 37, which occupies at least a portion of the triangular cross section and may extend the entire length of the beam. The presence of interior cavity 37 is advantageous in that it facilitates influx of air via air feed tube 8 to the conglomerate and drainage of excess fluids. Also, the weight of each beam 24 is consequently reduced, its weight being even further reduced when made of fiberglass, so that it can be easily manipulated. Thus a beam can be modular in the sense that a beam section having a length of approximately 40 cm can be coupled or detached from an adjacent section in accordance with the length of drum 5 and connected to drum inner surface 21. Furthermore, the reduced-weight beam 24 reduces the resistance of rotating drum 24, and therefore provides energy savings.

Shaftless screw conveyor 22, which may be made of fiberglass, is configured with a continuous helical profile having for example a lead angle of 4.5 degrees and a helix angle of 2-5 degrees. The radially outward edge 31 of each flight 28 of shaftless screw conveyor 22 is connected to inner surface 21 of drum 5. In order to accommodate the presence of cantilevered triangular blade 34 of each reinforcement beam 24, the radially outward edge 31 of each flight 28 is configured with a triangular cutout 33 by which the flight is connected to the cantilevered triangular blade. A cross member 26 may longitudinally extend between, and increases the structural strength of, adjacent flights 28. Since screw conveyor 22 is connected to inner surface 21 of drum 5 to facilitate rotation about its longitudinal axis together with the drum, its radially inner edge 27 needs not to be connected to a shaft and is therefore unobstructed, to provide the advantages described hereinabove.

An important aspect of the invention is the ability of the processor to ensure that all insect larvae located within each rearing chamber will be characterized by a substantially uniform developmental stage that is different from the development stage of the insect larvae located in an adjacent rearing chamber. Since the insect larvae are progressively more developed within more distally located rearing chambers, the processor may advantageously continuously harvest the insect larvae for protein insofar as a fresh supply of conglomerate is able to be introduced simultaneously with the discharge of the fully developed insect larvae.

Provision of substantially uniformly developed insect larvae within a given rearing chamber is made possible by virtue of the circumferentially spaced cantilevered triangular blades 34.

Two adjacent, longitudinally spaced flights 28 of screw conveyor 22 define therebetween the longitudinal length of a rearing chamber R for the insect larvae. Since the flights 28 of screw conveyor 22 are substantially mutually parallel, being oriented substantially perpendicularly to the drum's longitudinal axis, and occupy substantially the interior cross section of drum 5, and since radially outward edge 31 of each flight 28 is fixed to the drum inner surface 21, the mobility of the insect larvae is significantly limited to prevent passage of the insect larvae from one rearing chamber to another.

The useful volume of rearing chamber R is defined by the triangular blades 34, which firmly hold, and pierce to a certain extent, a portion of the conglomerate which has been introduced into the rearing chamber R. Since the semisolid conglomerate has sufficient structural strength to support its own weight when held by the blades, a conglomerate portion located between two adjacent blades 34 will not separate from the other conglomerate mass and fall to the inner surface of drum 5. A typical useful volume of a rearing chamber R is 6-7 $m^3$ for a 25-m long drum and a screw diameter of 1.25 m.

By firmly holding the introduced conglomerate portion, the circumferentially spaced blades 34 ensure that the conglomerate portion will remain substantially unified throughout its residing time within drum 5, ranging for example 12-20 days. During rotation of drum 5, the same conglomerate portion held by a set of blades 34 is urged along a specific helical path characterized by upward rotational movement followed by downward rotational movement to advance distally within the drum interior. Even following downward rotational movement under the influence of gravity, the blades 34 engage the conglomerate portion from below to prevent a significant majority thereof, e.g. 75-80%, from becoming disintegrated throughout the drum interior and from becoming ejected to a neighboring rearing chamber.

The conglomerate portion undergoes a mixing action while being displaced along the specific helical path. The mixing action results from a combination of the upward and downward rotational movement the conglomerate portion while being held by a plurality of blades 34, and of larval activity characterized by actively burrowing within the substrate. These two factors both help to produce a substantially uniform and homogeneous distribution of nutrients, substrate and insect larvae in a way that will make the biowaste processing operation more efficient.

This process repeats itself during each revolution of the screw conveyor to facilitate longitudinal conveyance of a conglomerate portion throughout the length of the drum. As the conglomerate portion is conveyed to a more distally located rearing chamber, the insect larvae digest additional biomass, causing the mass of the biomass to be reduced while the size of the insect larvae is increased. The insect larvae exhibit a biowaste reduction capacity ranging from 50-70% at an extreme proximal rearing chamber relative to an extreme distal rearing chamber. As a result of the metabolic and digestive activities of the insect larvae and of evaporation due to heat generated during the biowaste processing operation, the liquid content of the conglomerate portion is reduced from 50-70% at the extreme proximal rearing chamber, a value which is required by the insect larvae to ensure normal activity, to 20-40% at the extreme distal rearing chamber. The plurality of blades 34 are able to continue holding and gripping the conglomerate portion despite a reduction in its volume and in its water content and its downward rotational movement. Consequently, the insect larvae found in a given rearing chamber are of a same developmental stage and gain weight at a substantially uniform rate.

Figure 8:
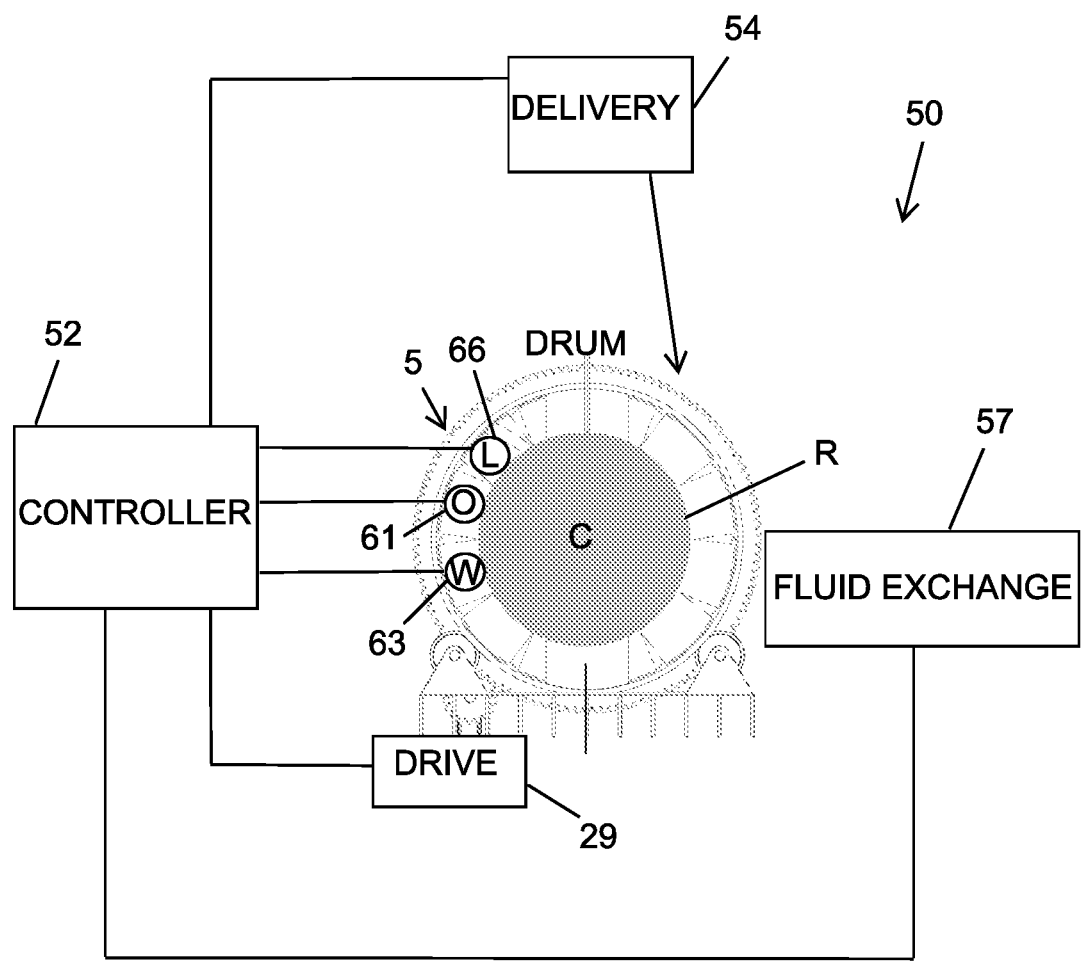
FIG. 8 is a schematic illustration of a control system used in conjunction with the biowaste processor of FIG. 1.

FIG. 8 schematically illustrates a control system 50 for monitoring biological and physical parameters of importance that are associated with a given conglomerate portion C received in a rearing chamber.

Control system 50 comprises controller 52 located externally to drum 5, and delivery mechanism 54 for delivering the conglomerate C to a proximal rearing chamber, whose operation is controlled by controller 52.

Delivery mechanism 54 may be a weight controlled delivery mechanism that defines a weight to volume ratio based on the biowaste being processed and to thereby determine the volume of the conglomerate to be introduced into the proximal rearing chamber. For example, the specific gravity of 25%-solid sewage sludge is different than 10% solids, and the specific gravity of agricultural waste is different than bakery waste etc. Based on the weight to volume ratio of the biowaste being processed, each conglomerate portion will be assigned an adjusted weight to volume ratio.

Controller 52 is also in electrical communication with motor drive 29 so that it will be commanded to drive drum 5 at a predetermined slow rate. Controller 52 may be a computerized control and control module which is configured to adjust the speed of drum 5 if necessary during the course of a processing operation, depending on data received from process related sensors, although the drum speed will not exceed a rate of one-half a revolution per hour. The plurality of sensors, including oxygen sensor 61, weight sensor 63 and liquid sensor 66, are provided within a given rearing chamber R and are in electrical communication with controller 52, preferably in wireless communication with controller 52. The sensors may be embedded in the drum inner surface, for example underneath a fiberglass element.

Controller 52 will command operation of a fluid exchange unit 57, e.g. a ventilation unit, if the oxygen level detected by oxygen sensor 61 deviates from a predetermined level. The ventilation unit is configured to ventilate the drum interior in addition to the conventional aeration of the conglomerate and dissipation of the generated process-derived heat, which result from rotation of drum 5.

Fluid exchange unit 57 generates gas inflow or outflow with respect to the drum interior, for example after high values of unwanted gases or low oxygen levels have been detected.

Figure 9:
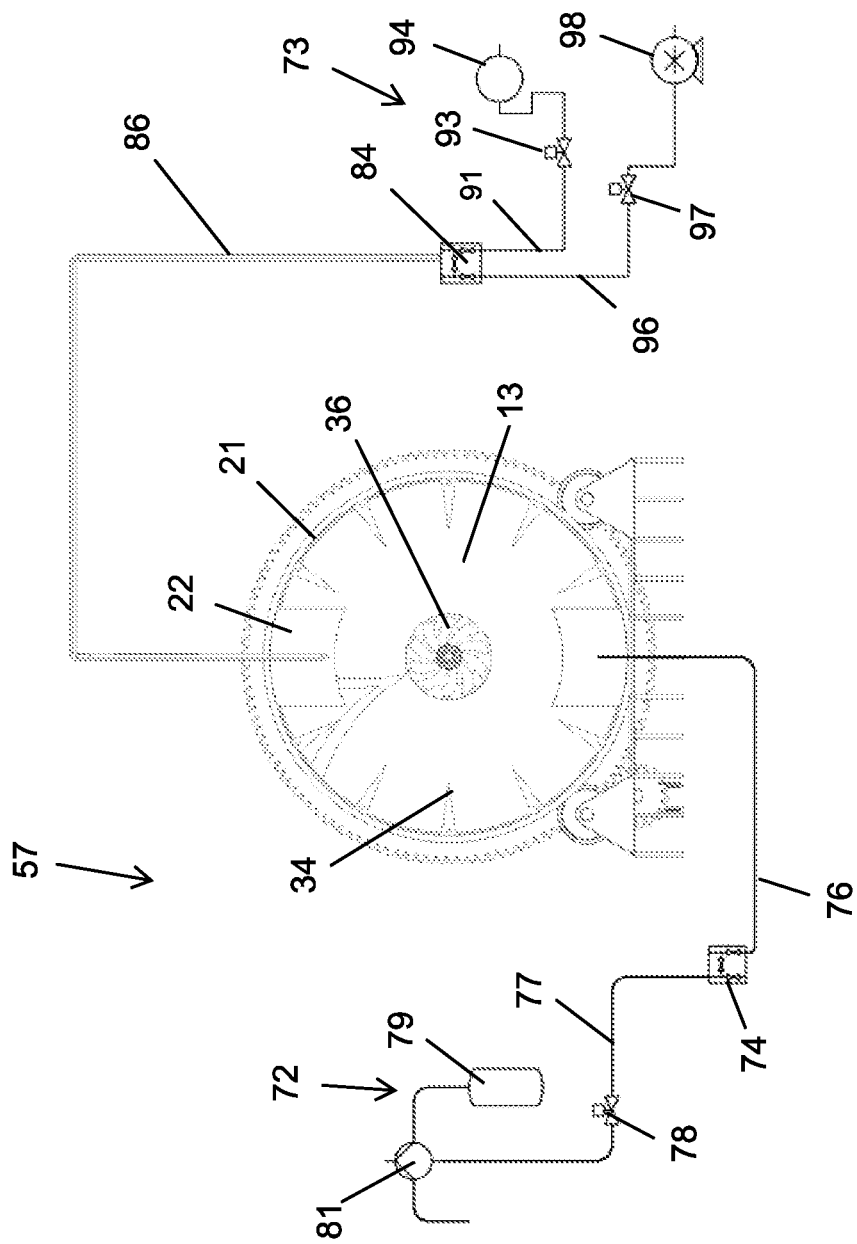
FIG. 9 is a schematic illustration of a fluid exchange unit used in conjunction with the biowaste processor of FIG. 1.

In one embodiment, as schematically illustrated in FIG. 9, fluid exchange unit 57 comprises two arrays 72 and 73 of valves, each of which is operatively connected proximate to a different region of screw conveyor 22. The two arrays 72 and 73 of valves may be diametrically opposed to each other, to allow an instantaneously downwardly positioned valve of the first array 72 to drain excess liquids while an instantaneously upwardly positioned valve of the second array 73 is able to perform a gas transfer operation. Each of the valves may be a unidirectional valve or an electrically controlled valve.

Screw conveyor 22 may be a hollow structure in addition to the triangular blades 34, in order to lower installation and production costs, as well as to facilitate efficient and easy maintenance. Accordingly, each valve may be mounted within a flight of the screw conveyor 22 and close to the inner drum surface 21, so as to be in fluid communication with the drum interior 13, cavity 37 and air feed tube 8 (FIG. 2).

The first array 72 comprises one or more valves 74 and a conduit 76 along which the exchanged liquid is able to flow. When valves 74 are unidirectional valves, some are adapted to allow only inflow of liquid into drum interior 13, and some are adapted to allow only outflow of liquid from drum interior 13. When valves 74 are control valves, they are adapted to be controllably openable and closable in response to sensed conditions. Another control valve 78 may be operatively connected to conduit 77 extending from a multi-passage flow junction 81 to the valves 74. Flow junction 81 may facilitate simultaneous liquid inflow and outflow, or alternatively facilitates only liquid inflow or only liquid outflow at any given time. Liquid outflow from drum interior 13 may be discharged to collection element 79, such as a drain.

The second array 73 comprises one or more valves 84 and an air tube 86 in fluid communication with each valve 84 and with the drum interior 13. When valves 84 are unidirectional valves, some are adapted to allow only inflow of air into drum interior 13, and some are adapted to allow only outflow of air from drum interior 13. When valves 84 are control valves, they are adapted to be controllably openable and closable in response to sensed conditions.

A common inflow line 91 to which are operatively connected control valve 93 and compressor 94 and a common outflow line 96 to which are operatively connected control valve 97 and vacuum pump 98 or other means for causing evacuation of gases from drum interior 13 are in fluid communication with each valve 84. Controller 52 (FIG. 8) will cause a control signal to one or more in order to correct the current oxygen level. For example, controller 52 will cause compressor 94 to be activated and the control valve 84 located proximate to the rearing chamber found to have a deviative oxygen level to be opened, in order to correct the current oxygen level.

Controller 52 may command operation of fan 36 and of one or more valves, so that the corresponding air inflow into the drum interior will propel and cause evacuation of excess gases. The air drawn through the fan may flow through an external filter to prevent inflow of malodorous gases and to filter out unwanted gases.

The volume and rate of gas exchange with respect to drum interior 13 are controlled by controller 52 in response to sensor readings, in order to optimize the biowaste processing operation. Various parameters that are fed to a self-learning computerized module include low oxygen level, high carbon dioxide level, ammonia levels, and low temperatures to regulate the volume and rate of gas exchange as well as the drum speed.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A continuous insect-based biowaste processor, comprising:
   a) a tubular drum having a longitudinal axis and an interior that is defined by a proximal inlet end and a distal outlet end;
   b) a drive for rotatably driving said drum about said axis;
   c) a shaftless screw conveyor fixedly connected to an inner surface of said drum;
   d) a plurality of circumferentially spaced cantilevered blades that are connected to said inner drum surface and that each longitudinally extend throughout said drum; and
   e) a delivery mechanism for introducing a conglomerate portion that includes biowaste and insect larvae into said inlet end of said drum interior,
   wherein said screw conveyor is subdivided into a plurality of longitudinally spaced rearing chambers for the introduced insect larvae, each of said rearing chambers being defined by two longitudinally adjacent flights of said screw conveyor and by said circumferentially spaced cantilevered blades, a first rearing chamber of said plurality of rearing chambers that is located closer to said outlet end than a second rearing chamber of said plurality of rearing chambers being defined as a more distally located rearing chamber relative to said second rearing chamber,
   wherein two or more of said circumferentially spaced cantilevered blades are configured to firmly hold and unify said conglomerate portion at any given instance throughout a residing time of said conglomerate portion within said drum interior,
   wherein said held conglomerate portion, during each rotation of said drum and of said screw conveyor connected thereto, is urged along a specific helical path characterized by upward rotational movement followed by downward rotational movement to advance distally within said drum interior from said inlet end to said distal outlet end and is engaged from below by said two or more circumferentially spaced cantilevered blades to mitigate disintegration of said held conglomerate portion, and
   wherein mass of the biowaste of said held conglomerate portion is reduced as said held conglomerate portion is conveyed to the more distally located rearing chamber and the insect larvae digest additional biowaste while increasing in size, the size of the insect larvae progressively increasing within the more distally located rearing chamber.

2. The biowaste processor according to claim 1, wherein a fresh supply of conglomerate containing young insect larvae is introducible into a proximal rearing chamber simultaneously with discharge of fully developed insect larvae from a distal rearing chamber.

3. The biowaste processor according to claim 1, wherein each of the cantilevered blades is configured with a triangular cross section.

4. The biowaste processor according to claim 3, wherein each of the cantilevered blades comprises a support beam connected to the inner drum surface and a triangular tip connected to the support beam.

5. The biowaste processor according to claim 1, wherein each of the cantilevered blades is longitudinally modular.

6. The biowaste processor according to claim 1, wherein each of the cantilevered blades is configured with an interior cavity.

7. The biowaste processor according to claim 1, further comprising an air feed tube in fluid communication with each of the cantilevered blades to facilitate influx of air into the drum interior.

8. The biowaste processor according to claim 1, further comprising a control system for monitoring parameters of importance that are associated with the conglomerate portion received in one of the rearing chambers and for adjusting a value of one or more of the parameters that has been found to be deviative.

9. The biowaste processor according to claim 8, wherein the control system comprises a controller in data communication with the drive, to regulate a rotational speed of the drum to be no more than one-half a revolution per hour.

10. The biowaste processor according to claim 9, wherein the rotational speed of the drum is regulated to range from 1 to 10 revolutions per day.

11. The biowaste processor according to claim 9, wherein the control system further comprises a fluid exchange unit for generating gas inflow or outflow with respect to the drum interior.

12. The biowaste processor according to claim 11, wherein the fluid exchange unit comprises two arrays of valves, each of which operatively mounted proximate to a different region of the inner drum surface, an air tube in fluid communication with each of the valves, and a compressor.

13. The biowaste processor according to claim 12, wherein each of the valves is a unidirectional valve.

14. The biowaste processor according to claim 12, wherein each of the valves is an electrically controlled valve.

15. The biowaste processor according to claim 14, wherein the controller is operable to cause the compressor to be activated and one of the valves proximate to a rearing chamber found to have a deviative oxygen level to be opened, in order to correct a current oxygen level.

16. The biowaste processor according to claim 14, wherein the fluid exchange unit comprises a fan and the controller is operable to command operation of the fan and of one or more of the valves, so that corresponding air inflow into the drum interior will propel and cause evacuation of excess gases through the one or more valves.

17. The biowaste processor according to claim 9, wherein the controller is a self-learning control module.

18. The biowaste processor according to claim 1, wherein the size of the insect larvae in each of the plurality of rearing chambers is uniform.

19. The biowaste processor according to claim 1, wherein the held conglomerate portion has a uniform and homogeneous distribution of nutrients, biowaste and insect larvae as a result of the upward rotational movement and downward rotational movement of the held conglomerate and of larval activity within the held conglomerate portion characterized by active burrowing therewithin.

* * * * *